(12) United States Patent
Vester

(10) Patent No.: US 7,573,036 B2
(45) Date of Patent: Aug. 11, 2009

(54) METHOD AND APPARATUS FOR PROCESSING OF DETECTOR SIGNALS

(75) Inventor: Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 282 days.

(21) Appl. No.: 11/602,211

(22) Filed: Nov. 21, 2006

(65) Prior Publication Data

US 2007/0114423 A1 May 24, 2007

(30) Foreign Application Priority Data

Nov. 22, 2005 (DE) .................. 10 2005 055 656

(51) Int. Cl.
*G01T 1/20* (2006.01)
*G01T 1/164* (2006.01)
*G01T 1/166* (2006.01)
(52) U.S. Cl. .............. 250/369; 250/363.03; 250/363.04
(58) Field of Classification Search ................ 250/369, 250/363.03, 206.1, 208.1, 363.04; 375/317, 375/286, 287
See application file for complete search history.

(56) References Cited

U.S. PATENT DOCUMENTS

| 2,632,058 | A | | 3/1953 | Gray | |
|---|---|---|---|---|---|
| 5,428,215 | A | * | 6/1995 | Dubois et al. | ............. 250/206.2 |
| 5,525,803 | A | * | 6/1996 | Watanabe et al. | ........... 250/369 |
| 7,265,331 | B2 | * | 9/2007 | Muenter et al. | .......... 250/208.2 |

OTHER PUBLICATIONS

Kejzlar, Ludek; Fischer, Jan: "Signal Processing by Inherent FIR Filter in the Line CCD Sensor", Nové smery v spracovani signálov VI., Liptovský Mikulás, Slowakei: Military Academy, 2002, vol. 2, pp. 215-218, ISBN 80-8040-180-2.
Zarnowski, Jeffrey J.; Carbone, Joseph; Pace, M.: "Scientific CMOS CID Imagers", Solid State Sensor Arrays and CCD Cameras, San Jose, USA, Jan. 31-Feb. 2, 1996, Anagnostopoulos, Constantine N.; Blouke, Morley M.; Lesser, M.P. [Eds.]: Proc. SPIE, vol. 2654, Mar. 1996, pp. 29-37.
Gruev, Viktor; Etienne-Cummings, Ralph: "Implementation of Steerable Spatiotemporal Image Filters on the Focal Plane", IEEE Transactions on Circuits and Systems—II: Analog and Digital Signal Processing, vol. 49, No. 4, Apr. 2002, pp. 233-244.
Hering, Ekbert; Gutekunst, Jürgen: Dyllong, Ulrich: .Informatik für Ingenieure, Düsseldorf: VDI-Verlag, 1995. ISBN 3-18-400944-0, Abschnitt A 4.4.2: Gray-Kode, S. 41-44.
Gühring, Jens: "Reliable 3D Surface Acquisition, Registration and Validation using Statistical Error Models", 3DIM 2001, Quebec City, Kanada, 2001, Conference Proceedings, pp. 224-231.

(Continued)

*Primary Examiner*—David P Porta
*Assistant Examiner*—Faye Boosalis
(74) *Attorney, Agent, or Firm*—Harness, Dickey & Pierce, P.L.C.

(57) ABSTRACT

A method and an apparatus are disclosed for processing of detector signals, for example in nuclear-medical imaging. In at least one disclosed embodiment, the signals from N photodetectors are transmitted to a total of approximately M=ld (N) output lines, with the signals from the photodetectors each being weighted with +1 or −1 for the addition onto an output line.

24 Claims, 4 Drawing Sheets

OTHER PUBLICATIONS

Symonds-Tayler, J.R.N.; Reader, A.j.; Flower, M.A.: "Design and Performance of an Acquisition and Control System for a Positron Camera with Novel Detectors", IEEE Transactions on Nuclear Science, vol. 44, No. 4, Aug. 1997, pp. 1527-1532.

Garcia, Ernest V.; Faber, Tracy L.; Galt, James R.: "Advances in Nuclear Emission PET and SPECT Imaging", IEEE Engineering in Medicine and Biology Magazine, vol. 19, No. 5, Sep.-Oct. 2000, pp. 21-33.

Raheja, Amar; Doniere, Timothy F.; Dhawan, Atam P.: "Multiresolution Expectation Maximization Reconstruction Algorithm for Positron Emission Tomography using Wavelet Processing", IEEE Transactions on Nuclear Science, vol. 46, No. 3, Jun. 1999, pp. 594-602.

German Office Action dated Feb. 22, 2006.

Kejzlar, Ludek; Fischer, Jan: Signal Processing by Inherent FIR Filter in the line CCD Sensor. In:Nové smery v spracovaní signálov VI., Liptovsky Mikulás, Slowakei: Military Academy, 2002, vol. 2, pp. 215-218. ISBN 80-8040-180-2.

Zarnowski, Jeffrey J.; Carbone, Joseph; Pace, Matt: Scientific CMOS CID Imagers. Solid State Sensor Arrays and CCD Cameras, San Jose, USA Jan. 31-Feb. 2, 1996. Anagnostopoulos, Constantine N; Blouke, Morley M.; Lesser, M.P. [Eds.]: Proc. SPIE, vol. 2654, Mar. 1996, pp. 29-37.

Gruev, Viktor; Etienne-Cummings, Ralph: Implementation of Steerable Spatiotemporal Image Filters on the Focal Plane. IEEE Transactions on Circuits and Systems—II: Analog and Digital Signal Processing, vol. 49, No. 4, Apr. 2002, pp. 233-244.

Hering, Ekbert; Gutekunst, Jürgen; Dyllong, Ulrich: Informatik für Ingenieure. Düsseldorf: VDI-Verlag, 1995. ISBN 3-18-400944-0. Abschnitt A 4.4.2: Gray-Kode, S. 41-44.

Gühring, Jens: Reliable 3D Surface Acquisition, Registration and Validation using Statistical Error Models. 3DIM 2001, Quebec City, Kanada, 2001. Conference Proceedings, pp. 224-231.

Symonds-Tayler, J.R.N.; Reader, A.J.; Flower, M.A. et al.: Design and Performance of an Acquisition and Control System for a Positron Camera with Novel Detectors. IEEE Transactions on Nuclear Science, vol. 44, No. 4, Aug. 1997, pp. 1527-1532.

Garcia, Ernest V.; Faber, Tracy L.; Galt, James R. et al.: Advances in Nuclear Emission PET and SPECT Imaging. IEEE Engineering in Medicine and Biology Magazine, vol. 19, No. 5, Sep.-Oct. 2000, pp. 21-33.

Raheja, amar; Doniere, Timothy F.; Dhawan, Atam P.: Multiresolution Expectation Maximization Reconstruction Algorithm for Positron Emission Tomography using Wavelet Processing. IEEE Trasactions on Nuclear Sciene, vol. 46, No. 3, Jun. 1999, pp. 594-602.

* cited by examiner

METHOD AND APPARATUS FOR PROCESSING OF DETECTOR SIGNALS

PRIORITY STATEMENT

The present application hereby claims priority under 35 U.S.C. §119 on German patent application number DE 10 2005 055 656.6 filed Nov. 22, 2005, the entire contents of which is hereby incorporated herein by reference.

FIELD

The invention generally relates to a method and/or an apparatus for processing of detector signals in nuclear-medical imaging. For example, the method and apparatus can be used for processing of the signals from photodetectors in a PET camera which is arranged in an MR magnet.

BACKGROUND

The aim of nuclear-medical imaging is to display physiological and biochemical processes within the body. The patient is in this case given a tracer with a radionuclide, which is distributed in the body and in this case emits radioactive radiation. This radiation is measured using a camera which contains suitable detectors, and the tracer distribution in the body is determined in this way.

In the case of positron emission tomography (PET), positron emitters are used as tracers and emit positrons which decompose in the body into two opposing Gamma quanta. In the case of SPECT (Single Photon Emission Computed Tomography) imaging, in contrast, gamma emitters are used as radionuclides. In both cases, the gamma quanta are trapped, for example, by a matrix of scintillation crystals, in which an impacting photon produces a light flash. This is in turn trapped and amplified by photodetectors, for example by photomultiplier tubes (PMT) or avalanche photodiodes (APD).

Each detector is followed by electronic pre-amplification and filtering of the signals, which are then passed in parallel via a cable harness to the downstream evaluation units (trigger, time and amplitude characterization, energy selection coincidence detector).

Thus, in the known systems, the output signal from each photodetector is carried on a separate signal line. When a PET camera is installed in an MR magnet, a very large number of signal lines must therefore be routed out of the magnet bore in parallel. Since the lines are coupled to the radio-frequency and gradient fields of the MR system, this can lead to signal corruption. Digital processing of the events directly in the magnet will admittedly greatly reduce the amount of information and the number of lines. However, this is virtually impossible in practice because the MR antennas are highly sensitive to interference injected from clock and data signals.

So-called optical multiplexing is already known in order to reduce the number of signal lines in nuclear medicine. In this case, the spatial resolution of the camera is enhanced by way, for example, of a block with a large number of scintillation crystals acting via a light distributor on a group of only four photodetectors, which are fitted at the corners of the block. The light flash which is initiated by a radiation quantum is thus distributed over different photodetectors. A centroid, which corresponds to the location of the absorption of the quantum can be calculated from the signal level of the individual photodetectors. There are a plurality of variants of this method:

In the case of a block detector, one group of four photodetectors is fitted at the corners of a block of, for example, 8×8 crystal segments. The sum of the detector signals indicates the event energy, and the coordinates of the active pixel within the block can be calculated from the difference signals, if necessary after calibration of the position relationship (Anger camera principle).

In the case of a panel detector, there is no optical isolation between the blocks, and the light can be distributed over a plurality of photodetectors located in the vicinity. The intensities result from the position of the active pixel, convolved with a spatial impulse response of the light distributor. One advantage over the block principle is that the sensitivity range of a detector is not artificially restricted to two of four incident quadrants, that is to say all four adjacent blocks are covered. In consequence, only one fourth of the number of detectors required in the case of a block detector are required for a given resolution (for example one detector for 64 pixels).

The number of pixels which can be resolved per photodetector cannot, however be increased indefinitely because of the finite accuracy of the pulse amplitude measurement (photon statistics, detector and amplifier noise).

Methods for combination of the signals from a plurality of detectors onto as few signal lines as possible have already been developed, for example for video cameras. Since these measures do not, however, have to operate in strong magnetic fields, as in the case of a PET camera in an MR magnet, more complicated signal processing methods can be used here. One such method is disclosed, for example, in Kejzlar, Ludek; Fischer, Jan; "Signal Processing by Inherent FIR Filter in the Line CCD Sensor" In: Nové smery v spracovani signálov VI. Liptovský Mikuláš, Slowakei, Military Academy, 2002, vol. 2, pp. 215-218.

Frank Gray developed the so-called Gray code as an alternative to normal binary code, see U.S. Pat. No. 2,632,058. The Gray code was used, because it involved only single steps, as early as when finding a solution to the correspondence problem in the calculation of 3D coordinates with the aid of photogrammatic techniques from image data acquired using cameras for reliable inspection of industrial parts, see Gühring, Jens; "Reliable 3D Surface Acquisition, Registration and Validation using Statistical Error Models". 3DIM 2001, Quebec City, Canada, 2001. Conference Proceedings, pp. 224-231.

One example of a detector arrangement for a PET camera or SPECT camera with photodetectors, scintillation crystals (LSO crystals) and optical fibers is described in Garcia, Ernest V.; Faber, Tracey L.; Galt, James R. et al.: Advances in Nuclear Emission PET and SPECT Imaging. IEEE Engineering in Medicine and Biology Magazine, Vol. 19, No. 5, September-October 2000, pp. 21-33.

SUMMARY

In at least one embodiment of the invention, a method and/or an apparatus is provided, by which the signals from a plurality of detectors in a SPECT or PET camera can be combined on as few signal lines as possible.

To be precise, in the case of at least one embodiment of the invention, the signals from N detectors are transmitted to a total of M<N output lines, with the signal from each detector being added onto each output line and being weighted with a predetermined factor before addition. To be precise, the signals from the N photodetectors are transferred to a total of approximately or precisely M=ld(N) output lines and weighted in the process with +1 or −1 in accordance with a binary code. The symbol ld represents the dual logarithm, ld(N)=ln(N)/ln(2)=log(N)/log(2). By way of example, the dual logarithm of 4 is thus 2, and the dual logarithm of 16 is 4.

At least one embodiment of the invention thus allows the signals from a large number of photodetectors to be combined on a small number of signal lines. The weighting with +1 or −1 makes it possible not only to calculate back the position of the photodetectors producing the signal but also to estimate the energy of the initiating event from the signal levels on the output lines. Signals from a large number of photodetectors are combined on a small number of signal lines. The preferred weighting +1 or −1 makes it possible to calculate back the position of the photodetectors producing the signal but also to estimate the energy of the initiating event from the signal levels on the output lines.

At least one embodiment of the invention is particularly advantageous in those applications in which, as in the case of a SPECT or PET examination, only one signal-initiating event generally takes place at any given time. In the case of a PET examination, for example, at most two opposite pixels in the PET detector are virtually ever active at the same time, owing to the low radiation activity. Thus, in principle, detector signals can be electrically combined within a multiplex array. Seen from any desired Voxel in the patient, a multiplex array such as this in the case of PET may comprise at most one hemisphere.

At least one embodiment of the invention makes it possible to drastically reduce not only the number of connection lines but also the technical complexity for the required post-processing units.

It is particularly preferable for the detector signals to be weighted using the Gray code. The Gray code is another representation form of the binary code. It is based on two adjacent numbers not being able to differ by more than one bit.

As an example, the Gray code for N=8 detectors with the designations x=0 ... 7 is indicated in the following text. Since M=ld(N)=3, each detector is therefore allocated a three-digit Gray code, with which the corresponding detector signal is weighted, and is added to three signal lines (m=0 ... 2). The weighting makes use of +1 and −1 (instead of the actual digits 0 and 1 in the Gray code).

| g = | x = | Gray code |
|---|---|---|
| (+ + +) | 0 | 000 |
| (+ + −) | 1 | 001 |
| (+ − −) | 2 | 011 |
| (+ − +) | 3 | 010 |
| (− − +) | 4 | 110 |
| (− − −) | 5 | 111 |
| (− + −) | 6 | 101 |
| (− + +) | 7 | 100 |
| | m = 2 1 0 (=line number) | |

The Gray code can be calculated for each x and m by using the following formula:

$$g(x,m) = sgn(\cos((x+0.5)/2^m * pi/2)),$$

where sgn is the mathematical sign function. As can be seen from the above table, the most significant line (m=2) allows rough location, which is refined in binary steps by the further lines.

The method can also be used for two-dimensional detector arrays, in which the signals are processed separately on the basis of rows and columns in accordance with one example embodiment. In this case, each photodetector is allocated a Gray code on the basis of its x coordinate and a Gray code on the basis of its y coordinate, and the signal from the photodetector is added with a weighting which corresponds to the two Gray codes to a total of approximately $ld(N_y)+ld(N_x)$ output lines.

Optimum implementation of at least one embodiment of the invention is achieved when the signals from N detectors are combined onto exactly M=ld(N) signal lines, in which case it is also possible to provide a greater or lesser number of signal lines, for example additional test lines. The invention, in at least one embodiment, can likewise be transferred from the binary system to different numerical systems, for example with base 3 or 4.

The impact position of a radiation quantum within an arrangement of photodetectors can preferably be calculated from the signal levels of the output lines. If an optical multiplexing method as described above is used, the impact position can also be calculated within one block of pixels or scintillation crystals.

If the detector signals are added, this results in the problem that the uncertainty σ of the signal level measurement on an output line is increased by the added-noise contributions of the N−1 detectors that are currently not active, by a factor sqrt(N). In consequence, the determination of the location of the active pixel is considerably less accurate. In order to determine the energy, the magnitudes of the signal pulse levels could admittedly be averaged over the fully driven lines, but with only a much smaller factor sqrt(M−1) nevertheless being recovered in this way.

In order to avoid the noise contributions from the non-active detector channels, also referred to as input lines, the signals from the detectors are preferably predistorted before the weighted summation process electronically by way of a non-linear, expanding characteristic. For example, in the case of a square characteristic $u2=u1^2$, the standard deviation of the output signal σ2 is weighted by the noise at the input σ1 with the signal voltage itself, in accordance with:

$$\sigma 2 = \sigma 1 * du2/du1 = \sigma 1 * 2u1$$

Thus, the noise at the summation point is dominated by the currently active channel with a high drive level, while the basic noise on the non-active channels is suppressed. The non-linearity can then be calculated back again using hardware or software, with the reciprocal function, in order to determine the energy and to interpolate the location.

Alternatively, a threshold which passes on pulses and noise to the weighting nodes only above a certain minimum amplitude, is suitable for use as a non-linear characteristic. This can be provided particularly easily by means of a diode.

At least one embodiment of the invention is also directed at a corresponding apparatus in which the detector signals are carried on N input lines. Each input line is coupled to each of the M<N output lines in such a manner that the signal's from the photodetectors can be transferred with a predetermined weighting to the output lines. The apparatus is preferably suitable for carrying out the method as described above. It is particularly preferable to provide M=ld(N) output lines, onto which the signals from the detectors are transferred with a specific weighting based on the Gray code.

The input and output lines are preferably capacitively coupled to one another, although inductive coupling or other coupling is also feasible.

According to one example embodiment, the apparatus has a printed circuit board in which the input lines are routed in a first layer, and the output lines are routed in a second layer of the printed circuit board, which is separated by a shielding, with the shielding surface being broken through at each of the crossing points which are coupled to one another. Alternatively, the coupling can also be achieved without a shielding surface by broadening or narrowing the corresponding conductor tracks at the crossing points.

BRIEF DESCRIPTION OF THE DRAWINGS

Example embodiments of the invention will now be explained in more detail with reference to the attached drawings, in which.

DETAILED DESCRIPTION OF THE EXAMPLE EMBODIMENTS

Figure 1:
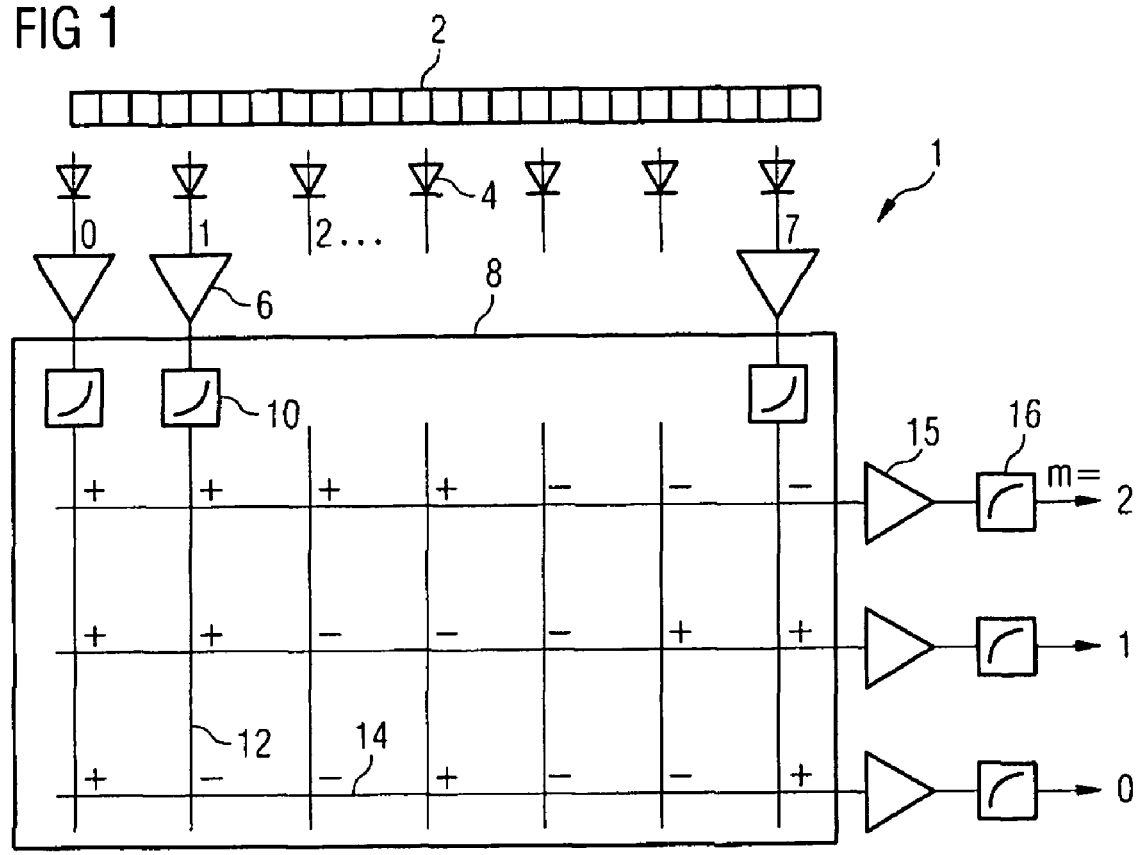
FIG. 1 shows a schematic illustration of one embodiment of the apparatus according to an embodiment of the invention.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows, schematically, the configuration of a gamma camera 1 with signal processing according to one example embodiment of the invention. The scintillation crystals 2 of the detector are in this case shown in the form of a one-dimensional array, for illustrative purposes, although the arrangement is generally two-dimensional. When a gamma quantum strikes a crystal 2 a light flash is produced which is detected by one or more of the photodetectors 4. In this schematic example, N=8 detectors are indicated, which may, for example, be avalanche photodiodes. The signals produced by these detectors 4 are amplified by preamplifiers 6 and are transferred to the output lines 14 in a weighting matrix 8, according to one embodiment of the invention.

Each detector signal is preferably amplified by an amplifier or a diode 10 with a non-linear characteristic in order to suppress the noise contributions of the non-active detector channels. The detector signals which are then applied to the input lines 12 are transferred to the M=3 output lines 14 with the weightings indicated by "+" and "−". The output signals which have been added up in this way are amplified by the output amplifiers 15, and are optionally subjected to a reciprocal of the non-linear characteristic 10 in the amplifier 16. The three outputs of the output lines are annotated m=2, 1 and 0.

Figure 2:
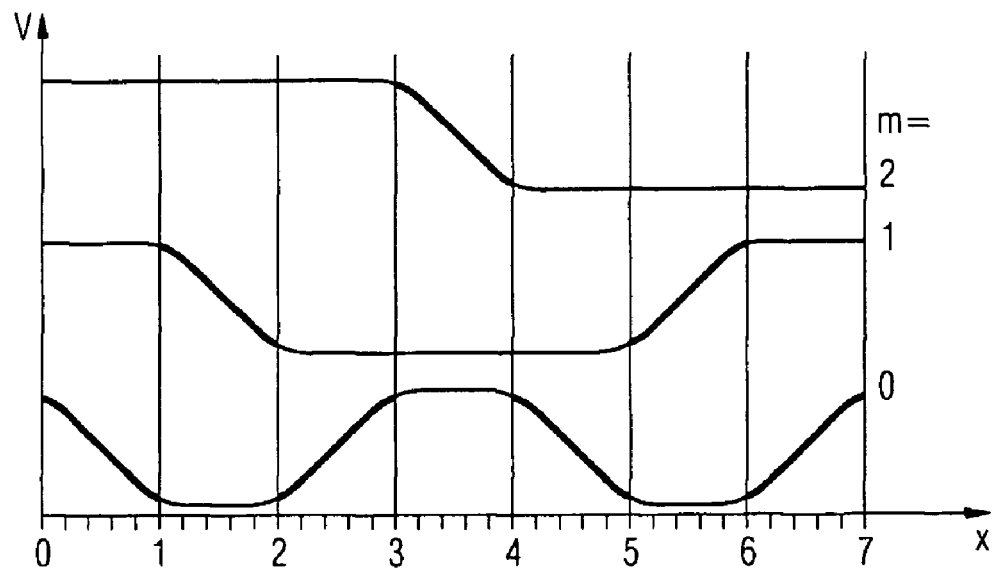
FIG. 2 shows a graph of the output voltages at the outputs illustrated in FIG. 1, as a function of the pixel location at which a radiation quantum is absorbed.

The pulses which come from the light detectors are unipolar (for example always negative). If only a single detector emits a pulse, this appears on each of the M output lines with a mathematical sign which indicates the corresponding weighting factor (+1 or −1). The mathematical signs of the pulses thus represent the address x of the active decoder in the Gray code.

in order to illustrate the effect of the Gray code which is used in the weighting matrix 8 in FIG. 1, reference is made to FIG. 2. FIG. 2 shows the weighting factors by which the signals from the photodetectors 4 at positions x=0 . . . 7 are multiplied before being fed into the output lines M=2, 1, 0. In this case, this shows the capability of the Gray code for location coding of the signals: output 2 is, for example, positive for x=0 . . . 3, while in contrast it is negative for the positions x=4 . . . 7. The line 2 thus allows rough allocation of a measured signal to a small or large x.

If a signal has been measured at this output which leads to the reduction of a positive weighting factor, only x=0 . . . 3 is possible for the position of the detector causing the signal. The output 1 has a positive weighting for x=0, 1, and a negative weighting for x=2, 3. A further restriction to two positions can thus be imposed by evaluation of this output within the first four positions. Finally, output 0 supplies the information for precise position determination of the detector which has detected the event which initiated the signal.

Figure 3:
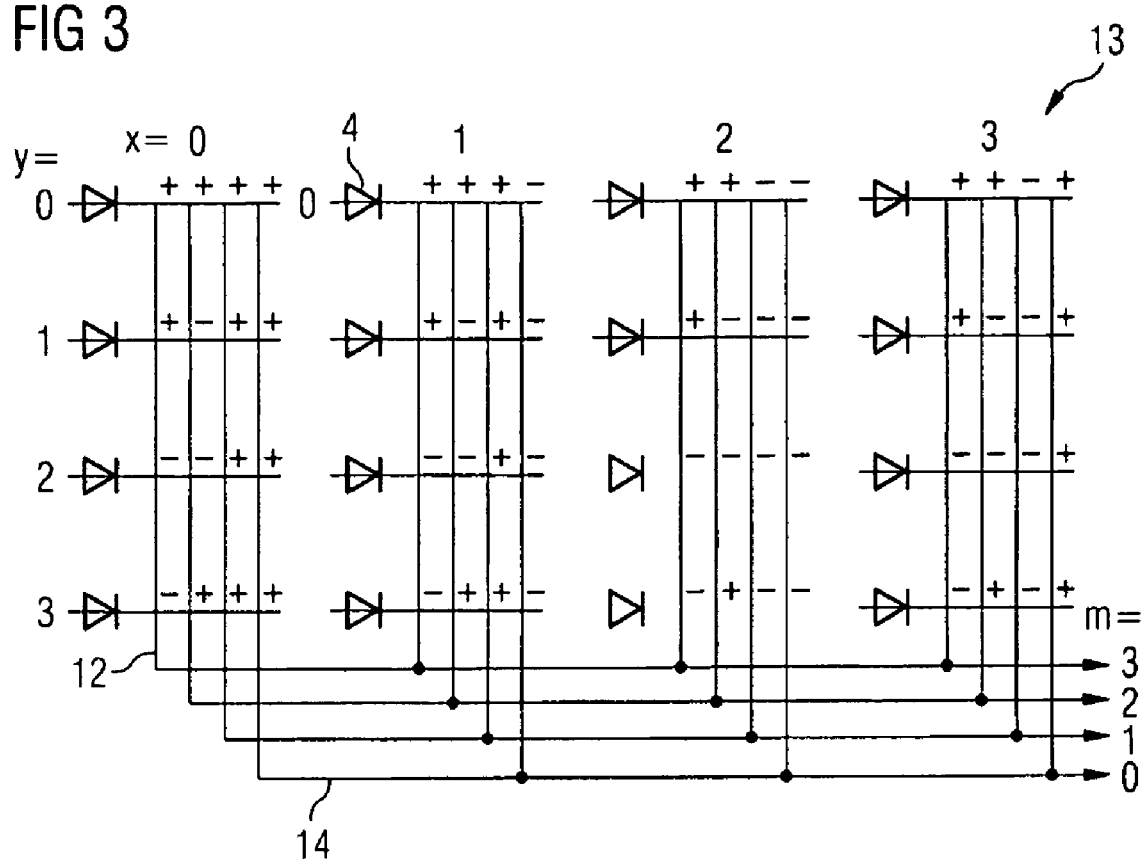
FIG. 3 shows a circuit diagram of a two-dimensional 4×4 detector matrix together with output lines according to one embodiment of the invention.

FIG. 3 shows a weighting matrix for a two-dimensional detector arrangement of 4×4 detectors. The detector crystals, amplifiers, etc. are not shown, for the sake of simplicity. Since $N_x$=4 columns and $N_y$=4 lines exist in this case, $ld(N_x)+ld(N_y)$=2+2 output lines are provided. The output lines 0, 1 represent the column address, and the output lines 2, 3 the row address.

In general, four adjacent detectors are activated with different amplitudes at the same time by the block-by-block optical multiplexing. In this case, the active block can then on the one hand be identified, and on the other hand, the position of the active pixel within the block can be identified.

The arrangement of the addresses using the Gray code has the important characteristic that only one line ever changes its mathematical sign when moving along one spatial direction between the adjacent addresses (pixel positions). A negative pulse of full amplitude (−E) is thus produced on some of the M lines and the maximum positive signal (+E) is produced on some of the others, with an intermediate value (−E<e<E) being produced only on a single line. If only the two values −E and +E are now used instead of the actual intermediate value for this line, this results in the Gray code addresses of the two adjacent detectors involved. The intermediate value itself is then used, in a known manner, by way of a previously calibrated position profile over dx=e/E for interpolation of the pixel location between these two detectors.

One example of a procedure for an evaluation process such as this will now be described with reference to FIGS. 3 and 4.

Figure 4:
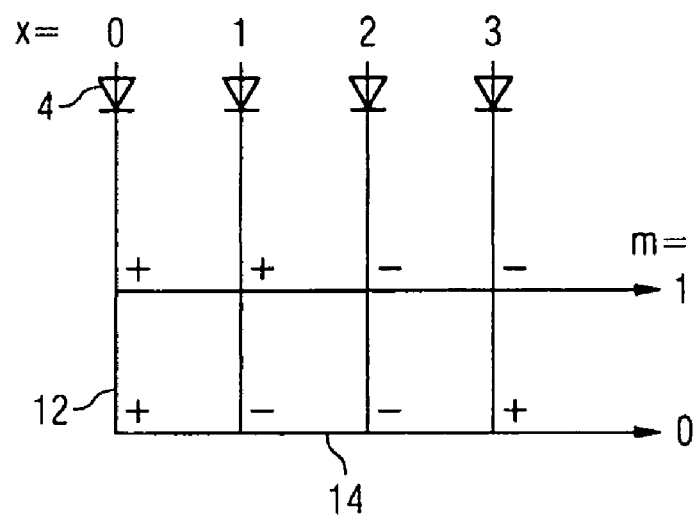
FIG. 4 shows a circuit diagram of a one-dimensional N=4 detector matrix together with output lines.

For simplicity, FIG. 4 shows a Gray code weighting matrix for four detectors in only one dimension. By way of example, a signal pulse with the following peak voltages is measured in the arrangement illustrated there:

| 1 | 0 | Line |
|---|---|---|
| +0.2 | +0.16 | Pulse level/Volts |

Line 1 shows the energy (−0.2V) via a weighting of −1, line 0 is in the transitional range. The two adjacent addresses are thus "−−" (x=2) and "−+" (x=3). The interpolation results in e/E=+0.16/−0.2=−0.8, that is to say 10% of the distance from 2 to 3, or x=2.5−0.8/2=2.1.

This example will now be extended to the two-dimensional arrangement in FIG. 3, in which the signals from 4×4 detectors are connected to four output lines. By way of example, a signal pulse with the following peak voltages is measured on these lines:

| 3 | 2 | 1 | 0 | Line |
|---|---|---|---|---|
| −0.2 | +0.08 | +0.2 | +0.16 | Pulse level/Volts |

The lines 0 and 1 give the x position. On the basis of the evaluation explained with reference to FIG. 4, the x coordinate of the active pixel is x=2.1.

The lines 3 and 2 give the y position. These indicate the transitional range between "++" (y=0) and "+−" (y=1), and e/e=−0.4 results in y=0.5+0.4/2=0.7. The uncalibrated pixel position is thus located at x=2.1, y=0.7 in the block at the top on the right. The active pixel location within the block can then be determined by association of the fractional component with the next pixel in the previously calibrated position profile.

In principle, the identification of the pixel position by way of the addresses of the adjacent detectors and interpolation between them operates both with and without subdivision of the array into blocks:

the adjacent address pairs do not all occur in the block-by-block arrangement, an active pixel can thus, for example, be located either between detector numbers 0 and 1 or between 2 and 3, but not between 1 and 2.

This restriction does not apply to the panel detector arrangement. Furthermore, detectors located further away may also still receive small light components, which leads to blurring of the transition between −E and +E. Nevertheless, the closest adjacent addresses can always be found by assuming the line with the smallest magnitude of the pulse level to be the transition and by interpreting the mathematical signs of the other lines as address bits. The accuracy of the interpolation can be improved somewhat further by detailed evaluation of the pulse levels on a plurality of lines.

Figure 5:
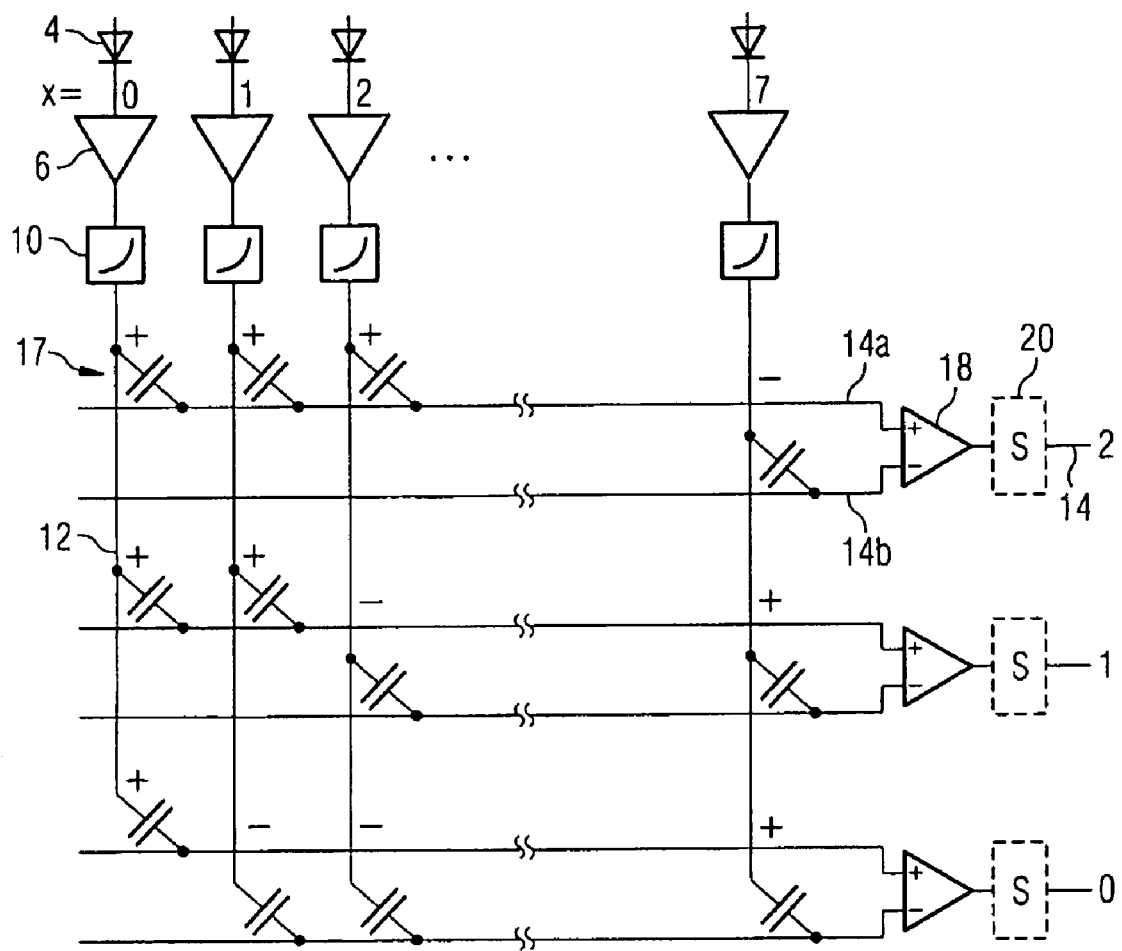
FIG. 5 shows a schematic illustration of capacitive coupling of input and output lines.

The combination of the N input lines of a detector array onto the M output lines requires N×M summation nodes, that is to say by way of example 2048 nodes for a large two-dimensional 16×16 array with 4+4 output lines. Capacitive coupling elements can be used, as shown in FIG. 5, in order to provide a low-cost, compact and low-noise weighting matrix. The input lines 12 coming from the preamplifiers 4 are coupled there by capacitors 17 to one of two lines in an output line pair 14a, 14b, to be precise to the line 14a for positive weighting, and to the line 14b for negative weighting. The voltages on one line pair 14a, 14b are subtracted from one another by means of the output differential amplifier 18, and form the output 14.

The capacitive coupling elements 17 have a high-pass filter character, which may be desirable for pulse steepening. This frequency response may, however, also optionally be compensated for by subsequent integration, for example, by connecting an integrating "charging-sensitive" amplifier 20 in-between.

Figure 6:
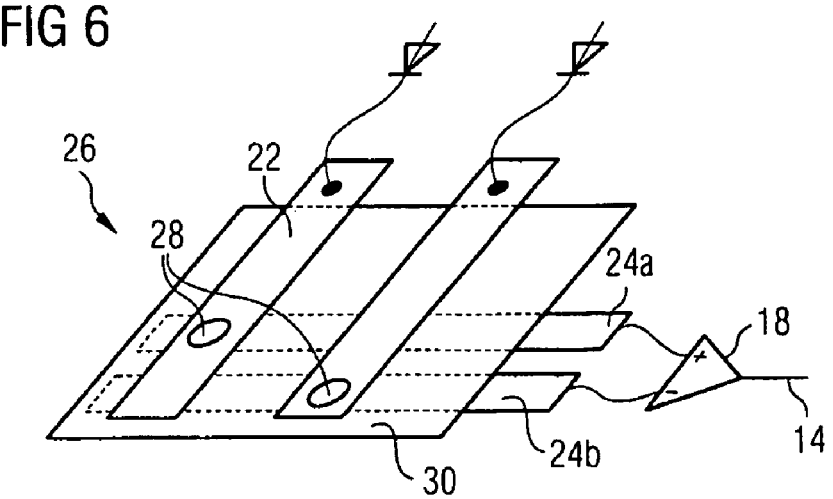
FIG. 6 shows a perspective illustration of a printed circuit board with input and output lines coupled according to one embodiment of the invention.
Figure 7:
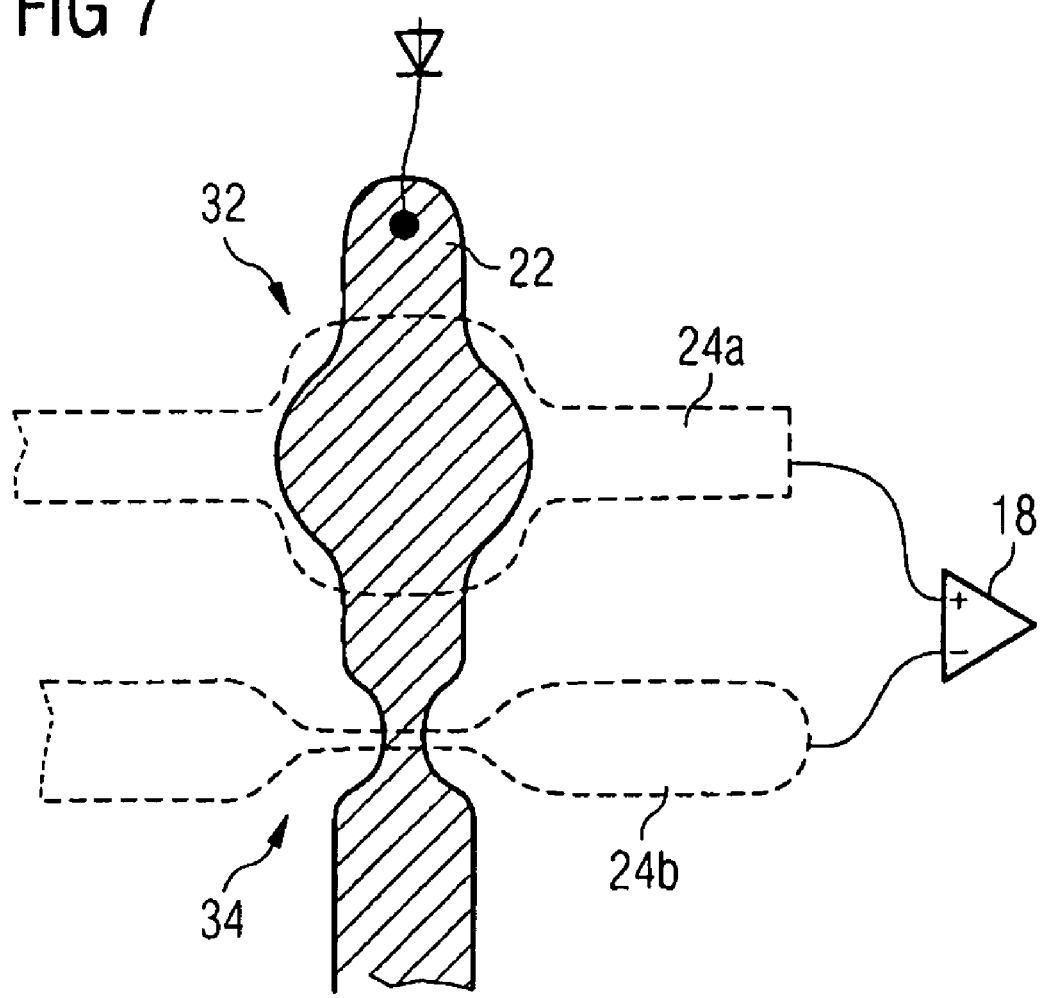
FIG. 7 shows a plan view of two crossing points of input and output lines, according to a further embodiment of the invention.

Instead of the capacitors 17, it is also possible to provide other capacitive coupling elements, as illustrated in FIGS. 6 and 7. Because of the short pulse rise times (a few nanoseconds), small capacitances (for example 1 pF) are sufficient and may, for example, be in the form of the coupling capacitance between two layers of a printed circuit board 26.

FIG. 6 shows a perspective view of a corresponding printed circuit board 26, which may form the main component of a signal processing apparatus. The 256 input lines, for example, of which only two are illustrated, run as conductor tracks 22 on one side of the printed circuit board 26. In a corresponding manner, eight differential output line pairs 14a, 14b run in a second layer on the other side of the board. Only one output line pair 24a, 24b is illustrated, for the sake of simplicity. A continuous shielding surface 30, which is interrupted by holes 28 at the crossing points which are intended to be coupled to one another, is located between the layers.

FIG. 7 illustrates an alternative coupling option for conductor tracks 22, 24. In this case, no shielding surface is provided, but only insulation between the input and output conductor tracks 22, 24, which run transversely with respect to one another. For unequal coupling to the two lines of the output line pair 24a, 24b, at least one of the input and output conductor tracks 22, 24 is broadened or narrowed at the crossing points. For example, a broadened area is provided at the crossing point 32 with the line 24a for positive weighting, and a narrowed area is provided at the crossing point 34 with the line 24b for negative weighting.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method to process detector signals in nuclear-medical imaging, comprising:
    transferring signals from N detectors to a total of approximately M=ld(N) output lines, with the signal from each detector being added to each output line and, before addition, being weighted with +1 or −1 in accordance with a binary code which is predetermined for each combination of a detector and output line.

2. The method of claim 1, wherein the binary code is a Gray code, in which two adjacent binary numbers differ by not more than one bit.

3. The method of claim 2, wherein, in the case of a two-dimensional matrix of $N_x \cdot N_y$ detectors in which the signals are processed separately on the basis of rows and columns, each detector is allocated a Gray code on the basis of its x coordinate and a Gray code on the basis of its y coordinate, and the signal from the detector is added with a weighting which corresponds to the two Gray codes to a total of $ld(N_y) + ld(N_x)$ output lines.

4. The method of claim 2, wherein two spatially adjacent detectors are each associated with two adjacent binary numbers.

5. The method of claim 1, wherein two spatially adjacent detectors are each associated with two adjacent binary numbers.

6. The method of claim 1, wherein an event measured by the detectors is located with only one event generally being processed at the same time.

7. The method of claim 1, wherein the detectors are photodetectors, and at least one detector is allocated to a block of scintillation crystals, connected via an optical fiber.

8. The method of claim 1, wherein the impact position of a radiation quantum within an arrangement of detectors is calculated from the signal levels on the output lines.

9. The method of claim 1, wherein the signals from the detectors are at least one of amplified and suppressed with a non-linear characteristic before the weighted addition onto the output lines.

10. The method of claim 1, wherein the method is used to process signals from photodetectors in a PET camera arranged in an MR magnet.

11. The method of claim 1, wherein the impact position of a radiation quantum within one block of scintillation crystals is calculated from the signal levels on the output lines.

12. The method of claim 1, wherein signals from the N detectors are transferred to a total of exactly M=ld(N) output lines.

13. The method of claim 12, wherein the symbol ld represents the dual logarithm, ld(N)=ln(N)/ln(2)=log(N)/log(2).

14. The method of claim 1, wherein the symbol ld represents the dual logarithm, ld(N)=ln(N)/ln(2)=log(N)/log(2).

15. An apparatus for processing detector signals in nuclear-medical imaging, comprising:
    N input lines, which carry the signals from N detectors as well as a total of approximately M=ld(N) output lines, with each input line being coupled to each output line in such a manner that the signals from the N detectors are added onto the M output lines with a weighting of +1 or −1, which is determined on the basis of a binary code.

16. The apparatus of claim 15, wherein each output line contains one output line pair, of which the signals weighted with +1 are transmitted on one line and the signals weighted with −1 are transmitted on the other line, with the two lines being connected to the one of two inputs of a subtractor and differential amplifier.

17. The apparatus of claim 15, wherein the input lines are capacitively coupled to the output lines.

18. The apparatus of claim 17, wherein the input lines are routed in a first layer of a printed circuit board, and the output lines are routed in a second layer of the printed circuit board, which is separated by a shielding surface, with the shielding surface being broken through at each of the crossing points which are coupled to one another.

19. The apparatus of claim 17, wherein the input lines are routed as conductor tracks in a first layer of a printed circuit board, and the output lines are routed as conductor tracks in a second layer of the printed circuit board, with the conductor tracks each being one of broadened and narrowed at the crossing points in order to achieve weighted coupling.

20. The apparatus of claim 15, wherein the apparatus is included in at least one of a SPECT and PET camera.

21. The apparatus of claim 15, wherein the binary code is a Gray code, in which two adjacent binary numbers differ by not more than one bit.

22. The apparatus of claim 15, wherein the total of output lines is exactly M=ld(N) output lines.

23. The apparatus of claim 22, wherein the symbol ld represents the dual logarithm, ld(N)=ln(N)/ln(2)=log(N)/log(2).

24. The apparatus of claim 15, wherein the symbol ld represents the dual logarithm, ld(N)=ln(N)/ln(2)=log(N)/log(2).

* * * * *